United States Patent [19]
Sakamoto et al.

[11] Patent Number: 5,049,309
[45] Date of Patent: Sep. 17, 1991

[54] TITANIA SOL

[75] Inventors: Masashi Sakamoto; Haruo Okuda, both of Yokkaichi; Setuo Koike, Suzuka; Yasuo Yamasaki, Yokkaichi, all of Japan

[73] Assignee: Ishihara Sangyo Kaisha, Ltd., Osaka, Japan

[21] Appl. No.: 98,463

[22] Filed: Sep. 18, 1987

[30] Foreign Application Priority Data

Sep. 22, 1986 [JP] Japan ................................. 61-224409
Nov. 12, 1986 [JP] Japan ................................. 61-268829
Feb. 17, 1987 [JP] Japan ................................. 62-33889

[51] Int. Cl.$^5$ .......................................... B01J 13/00
[52] U.S. Cl. .................. 252/313.1; 423/610; 424/59
[58] Field of Search ............... 252/313.1; 424/59; 423/610

[56] References Cited

U.S. PATENT DOCUMENTS

| | | | |
|---|---|---|---|
| 2,047,220 | 7/1936 | Patterson et al. | 106/18.31 |
| 2,448,683 | 9/1948 | Peterson | 423/616 |
| 3,098,044 | 7/1963 | Glover | 252/313 |
| 3,178,264 | 4/1965 | Sheehan et al. | 423/610 |
| 4,004,939 | 1/1977 | O'Brien et al. | 106/135 |
| 4,120,979 | 10/1978 | Schwarzmann et al. | 514/674 |
| 4,169,086 | 9/1979 | Nolken | 524/131 |
| 4,255,491 | 3/1981 | Igarashi | 427/144 X |
| 4,356,280 | 10/1982 | Wells et al. | 252/8.6 X |
| 4,442,252 | 4/1984 | Sumi et al. | 524/183 |
| 4,464,524 | 8/1984 | Karickhoff | 524/558 X |
| 4,547,546 | 10/1985 | Wells | 264/170 X |
| 4,612,138 | 9/1986 | Keiser | 252/313 |
| 4,612,354 | 9/1986 | Shimizu et al. | 526/62 |

FOREIGN PATENT DOCUMENTS 2194651 3/1974 France .
61-264063 11/1986 Japan ................................. 423/610

*Primary Examiner*—Robert L. Stoll
*Assistant Examiner*—Gary L. Geist
*Attorney, Agent, or Firm*—Cushman, Darby & Cushman

[57] ABSTRACT

Disclosed is a process for producing a titania sol which comprises an aqueous dispersion of finely-divided titania dispersed therein and has a neutral pH range. The process comprises peptizing hydrous titanium oxides with a monobasic acid or salt thereof to obtain an acidic titania sol and removing anions from the acidic titania sol.

6 Claims, No Drawings

TITANIA SOL

BACKGROUND OF THE INVENTION

This invention relates to a titania sol maintained at a stable dispersion state at a neutral pH range and a process for producing the same.

The titania sol of this invention can be adjusted to an optional pH range and furthermore finely-divided titania is maintained at a stable dispersion state in respective pH ranges. Therefore, the titania sol of this invention is suitable for various uses, for example, it is useful as raw materials for cosmetics and food packaging materials due to its ultraviolet ray screening effects.

In general, when a finely-divided titania powder, most particles of which have a size less than 0.1 $\mu$m, is incorporated into a resin film or molded product, the film or molded product transmits visible rays and screens ultraviolet rays to protect materials which may be disclored or deteriorated by irradiation with ultraviolet rays. Thus, such finely-divided titania powder has been used in plastic packaging materials for foods and medicines, plastic coating materials for agriculture and horticulture in facilities, cosmetic, etc. Usually, such finely-divided titania powder is produced by thermally hydrolyzing an aqueous titanium sulfate solution to precipitate agglomerated hydrous titanium oxides, neutralizing and washing the agglomerate, peptizing the agglomerate with addition of an acid such as hydrochloric acid or nitric acid to produce a titania sol having a pH of 3 or less, then neutralizing this sol and thereafter subjecting the sol to filtration, washing, drying and grinding (see U.S. Pat. No. 2,448,683).

Generally, a titania sol is stabilized in its dispersion state with acidic reagents such as hydrochloric acid and nitric acid and it shows an acidity of pH 3 or less and so is not suitable for uses in a wide range. In order to remove the acidic reagents and render the titania sol neutral, it can be considered to carry out neutralization-washing, ion exchange, ultrafiltration, etc., but these methods can damage the properties of titania sol such as dispersibility and it is difficult to obtain a neutral titania sol in stable dispersion. Therefore, in general, it is necessary to use an acidic titania sol as a dry powder prepared by subjecting the sol to neutralization, washing, drying and grinding. In this case, however, it is impossible to reproduce the dispersion state such as sol and thus characteristics of finely-divided particles cannot be fully brought about.

SUMMARY OF THE INVENTION

The inventors have made intensive researches in an attempt to utilize a titania sol for various uses with maintaining the good dispersion state as that of an acidic titania sol. As a result, it has been found that (a) when an acidic reagent in the acidic titania sol is removed by means such as ion exchange resins, ion exchange membranes and electrodialysis, gelation immediately occurs and finely-divided titania agglomerates, but when stirring is carried out for several hours thereafter, the finely-divided titania is unexpectedly redispersed, (b) when a water soluble organic compound such as polyvinyl alcohol or glycerin is added before or after the removal of the acidic reagent, there is obtained a titania sol in a uniformly dispersed stable state, (c) this titania sol has a neutral pH range and the stable state is still maintained after a pH has been changed in a wide range with addition of acidic reagents or alkaline reagents, and (d) such titania sol can readily be made into a paint film by mixing with various water soluble resins and the resulting film has ultraviolet absorption effects. This invention has been accomplished based on these findings.

DESCRIPTION OF THE PREFERRED EMBODIMENTS

The first invention concerns a titania sol which is an aqueous dispersion having a neutral pH range in which finely-divided titania is dispersed and the second invention is directed to a process for the production of the titania sol, which comprises peptizing hydrous titanium oxides with a monobasic acid or a salt thereof to obtain an acidic titania sol and removing anions from said acidic titania sol.

The titania sol of this invention is an aqueous dispersion having a neutral pH range of 6–8 in which finely-divided titania is dispersed. The titania sol of this invention may contain a dispersion-stabilizer for stabilizing the dispersion of finely-divided titania. Since the titania sol of this invention comprises finely-divided titania homogeneously dispersed in water and further the pH thereof can be optionally adjusted and a transparent paint film with maintaining a high dispersion state can be obtained therefrom by diluting the titania sol, if necessary, and then mixing with various resins, coating and drying the mixture, it can be used, for example, for a ultraviolet ray screening resin composition to be coated on the surface of food packaging materials. Further, the titania sol of this invention can be used in ultraviolet ray screening cosmetics by mixing with cosmetic chemicals.

The finely-divided titania which is a component of the titania sol of this invention means hydrous titanium oxides, e.g., amorphous oxides such as metatitanic acid or orthotitanic acid, partially-crystallized amorphous oxides containing a rutile or anatase type, or a mixture of both these amorphous oxides.

For example, when the titania sol is used for a ultraviolet ray screening resin composition, the finely-divided titania is preferably such that most of the particles (normally more than 80%) have a particle size 5 less than 0.1 $\mu$m. When the size is larger than said range or the particles are agglomerated, light-scattering effects of visible light increase to damage transparency.

The dispersion-stabilizers which may be added, if necessary, include water-soluble organic compounds and inorganic surface active agents. As the water-soluble organic compounds, there may be used water-soluble high molecular compounds such as polyvinyl alcohol, carboxymethyl cellulose, methyl cellulose, etc., nonionic surface active agents such as polyoxyethylene alkylphenyl ether compounds, polyoxyethylene alkyl ether compounds, polyoxyethylene fatty acid ester compounds, etc., cationic surface active agents such as fatty acid amines, quaternary ammonium salts, etc., polyhydric alcohols such as ethylene glycol, propylene glycol, butylene glycol, diethylene glycol, dipropylene glycol, triethylene glycol, 2-methyl-2,4-pentadiol, glycerin, etc. As the inorganic surface active agents, there may be used, for example, sodium pyrophosphate, sodium hexametaphosphate, sodium silicate, etc. The water soluble organic compounds are preferable to the inorganic surface active agents with reference to dispersion stabilizing effects. The water soluble high molecular compounds include those of various polymerization degrees. For example, polyvinyl alcohol of low polymerization degree can afford titania sols of a higher TiO2 concentration than that of high polymerization degree. Therefore, polyvinyl alcohol of about 500 in polymerization degree is preferred to that of 1900-2100 in polymerization degree. Among alcohols, monohydric alcohols such as methanol, ethanol, etc. can give, with difficulty, neutral sols stable in an area of a higher TiO2 concentration.

Concentration of finely-divided titania in the titania sol is suitably 1-40% by weight in terms of TiO2 considering production of sols in a stable dispersion state. Concentration of the dispersion-stabilizer is suitably 1-99% by weight.

The titania sol of this invention is maintained at a stable dispersion state in the neutral pH range and further is adjustable to an optional pH and depending on use and handling an acidic reagent or an alkaline reagent can be added or the sol can be heated in order to adjust the titania sol to the desired pH or concentration. If necessary, resins, colorants and/or the like may also be added.

The second invention provides a process for the production of the titania sol.

According to the process of this invention, firstly hydrous titanium oxides are subjected to peptization treatment with a monobasic acid or a salt thereof to produce an acidic titania sol. The hydrous titanium oxides are obtained, for example, by thermal hydrolysis or alkali neutralization of a titanium sulfate solution or titanium chloride solution. Hydrous titanium oxides obtained by the thermal hydrolysis of the titanium sulfate solution is usually subjected to neutralization with an alkaline reagent such as aqueous ammonia, filtration, washing and dehydration to remove the remaining sulfate radical as completely as possible and thereafter is subjected to peptization treatment with the addition of a monobasic acid such as hydrochloric acid, nitric acid, acetic acid, chloric acid, chloroacetic acid or the like. Alternatively, peptization treatment can be effected by adding to the hydrous titanium oxides a salt such as barium chloride which reacts with sulfate radical to produce an insoluble sulfate and simultaneously a univalent acid without the treatment of removal of sulfate radical by neutralization. The titania sol produced by peptization treatment contains a monobasic acid as a stabilizer and is ordinarily acidic and has a pH of 3 or less.

Secondly, anions in said acidic titania sol are removed, followed by stirring to obtain a titania sol. The removal of anions can easily be performed, for example, by an anion exchange resin, ion exchange membrane and electrodialysis. Due to the removal of anions the finely-divided titania in the sol tends to agglomerate, but homogeneous dispersion can be accomplished by continuation of stirring.

In the process of this invention, it is desirable to add a dispersion-stabilizer before or after the removal of anions in order to further improve the dispersion of finely-divided titania in sol. In this case, it is proper to add the dispersion-stabilizer of 1-100% by weight in concentration in such an amount that weight ratio to TiO2 is within the range of 0.05-10, preferably 0.1-5 for an acidic titania sol having a TiO2 concentration of 1-40% by weight. Thereafter, if necessary, the titania sol can be concentrated by heating. At the addition of the stabilizer, if a TiO2 concentration in the acidic titania sol is higher than said range, the sol in a stable dispersion state becomes difficult to obtain regardless of the concentration of the dispersion-stabilizer.

The removal of anions by an anion exchange resin, ion exchange membrane and electrodialysis can be performed by conventional methods. For example, as the anion exchange resins there may be used commercially available ones such as AMBERLITE IRA 400, AMBERLITE IRA 410, AMBERLITE IRA 910, etc. Addition amount of them may suitably be chosen depending on the desired amount of anions to be removed.

It is also possible to increase TiO2 concentration in titania sol by simultaneously carrying out the addition of acidic titania to dispersion-stabilizer and the removal of anions by an ion exchange resin, etc.

Especially when titania sol of rutile type is produced in this invention, it is desirable to employ the process according to which hydrous titanium oxides obtained by the neutralization of an aqueous titanium chloride solution such as an aqueous titanium tetrachloride solution with keeping pH at 7 or more with an alkali solution are heated in an acidic solution to obtain an acidic rutile type titania sol and thereafter anions are removed from this sol. It is also desirable for this process to add said dispersion-stabilizer before or after the removal of anions in the acidic sol in order to form a sol in a more stable dispersion state.

The process of this invention is characterized in that anions in acidic titania sol are removed by an anion exchange resin, ion exchange membrane, electrodialysis or the like and, if necessary, a dispersion-stabilizer is added before or after the removal of anions. According to the process of this invention, an acidic titania sol can be made to a titania sol showing stable dispersion in the neutral pH range. Further, this titania sol can be adjusted to a pH value in the alkaline pH range or the acidic pH range by the suitable addition of an alkaline reagent such as aqueous ammonia or an acidic reagent such as an aqueous hydrochloric acid solution.

The titania sol of this invention can readily be mixed with cosmetic bases or other cosmetic components because finely-divided titania is well dispersed in water. In addition, it has sufficient ultraviolet ray screening effect with a smaller addition amount than the conventional finely-divided titania powder and can afford markedly excellent transparency and is useful as cosmetic for sun care protection.

Amount of the titania sol in a cosmetic is 0.1-10% by weight, preferably 1-5% by weight in terms of TiO2.

The cosmetic may be any of a lotion type, cream type, paste type, stick type, etc.

EXAMPLES

A. Preparation of acidic titania sol

A titanium ore was reacted with sulfuric acid to obtain a titanium sulfate solution, which was then subjected to thermal hydrolysis to obtain an agglomerated metatitanic acid. An aqueous slurry of 30% by weight in terms of TiO2 was prepared therefrom and this slurry was adjusted to pH 7 with aqueous ammonia, then filtered and washed to remove sulfate. To the resulting dehydrated cake was added 35% hydrochloric acid to carry out peptization to obtain a titania sol of pH 1.5 and containing 1.5% by weight of HCl.

B. Preparation of neutral titania sol (a)

About 1000 g of an anion exchange resin (AMBERLITE IRA 910 manufactured by Tokyo Organic Chemical Ind. Ltd.) in a wet condition was rapidly thrown in 250 ml of the acidic titania sol (TiO2 30% by weight)

obtained in A above with well stirring and stirring was continued for about 4 hours. Thereafter, the anion exchange resin was removed by filtration to obtain a neutral titania sol (TiO2 20% by weight) of pH 7.8.

C. Preparation of neutral titania sol (b)

To 250 ml of the acidic titania sol obtained in A above was added 250 ml of commercially available glycerin, followed by adding about 1000 g of the same anion exchange resin as used above with stirring. After sufficient stirring, the anion exchange resin was removed by filtration to obtain a neutral titania sol (TiO2 12% by weight) of pH 7.2.

D. Heat concentration of neutral titania sol

The neutral titania sol (b) obtained in C above was concentrated by heating to 100° C. to obtain a stable sol containing 25% by weight of titania in terms of TiO2.

E. Preparation of neutral titania sol (c)

The procedure of C above was repeated, except that 250 ml of ethylene glycol was added in place of glycerin to obtain a neutral titania sol (TiO2 12% by weight) of pH 7.2.

F. Preparation of neutral titania sol (d)

The procedure of C above was repeated, except that the acidic titania sol was added to 250 ml of a polyvinyl alcohol (PVA) (polymerization degree 500) solution (PVA solid concentration 50 g/l) in place of glycerine to obtain a neutral titania sol (TiO2 2.4% by weight) of pH 7.2.

G. Preparation of neutral titania sol (e)

About 1000 g of the same anion exchange resin as used above was added to 250 ml of an acidic titania sol (TiO2 30% by weight). After well stirring, the anion exchange resin was removed by filtration, followed by adding 250 ml of glycerin to obtain a stable neutral sol (TiO2 12% by weight) of pH 7.8.

H. Test Example 1

The neutral titania sol (TiO2 12% by weight) obtained in C above was diluted to 0.1% by weight and charged in a quartz cell of 3 mm thick. Transmittance of this cell for visible light (550 nm) and ultraviolet ray (320 nm) was measured by UV-visible recording spectrophotometer (UV-240, Shimazu Corporation) to obtain 98% and 2%, respectively.

I. Test Example 2

The neutral titania sol (b) obtained in C above was mixed with the following components (2)–(4) and to the resulting mixture was added a mixture of the components (5) and (6) to homogeneously disperse them to obtain a cosmetic (sun care lotion).

| Components | Mixing ratio (% by weight) |
| --- | --- |
| (1) Neutral titania sol (TiO₂ 12% by weight) | 80 |
| (2) 1,3-butylene glycol | 3 |
| (3) Ethanol | 12 |
| (4) Perfume | Suitable amount |
| (5) Silicic anhydride | 3 |
| (6) Kaolin | 2 |

Thus obtained sun care lotion was coated at a wet film thickness of 12.7 μm on a triacetate film by a doctor blade of 0.5 mil. After air drying, transmittance of the film was measured by a UV-visible recording spectrometer (UV-240, Shimazu Corporation) to obtain the results as shown in the following table (Example).

| Wavelength (nm) | Transmittance (%) | | | | | | | |
| --- | --- | --- | --- | --- | --- | --- | --- | --- |
| | 700 | 600 | 500 | 400 | 350 | 325 | 300 | 275 |
| Example | 96.0 | 94.7 | 90.7 | 81.7 | 40.0 | 8.7 | 1.0 | 1.0 |
| Comparative Example | 88.7 | 85.0 | 78.3 | 63.0 | 13.0 | 1.0 | 1.0 | 1.0 |

(Note: In the above table, Comparative Example relates to a sun care lotion obtained by mixing the above components (2)–(4) with a mixture comprising 12% by weight of a finely-divided titanium dioxide powder having an average particle size of 0.03–0.05 μm, 58% by weight of distilled water and 30% by weight of glycerin in place of said neutral titania sol at the same mixing ratio as above and then mixing this mixture with said components (5) and (6) at the same mixing ratio as above.)

Conventional titania sols normally have an acidic pH range of 3 or less while maintaining the titania sol of this invention at a stable dispersion state at a neutral pH range and further its pH can be adjusted in a wide range. Thus, it is not limited in its use and can be utilized in a wide range of uses. Further, the titania sol is not gelled even when used under severe conditions and can be kept at a stable dispersion state. Moreover, the titania sol of this invention is stable against heat treatment and can be concentrated to a desired TiO2 concentration by suitable heating depending on the purpose and use.

What is claimed is:

1. A titania sol having a neutral pH range, comprising an aqueous dispersion containing more than 80% hydrous titanium oxide particles having a maximum particle size less than 0.1 μm and at lest one dispersion-stabilizer selected from water-soluble organic compounds and inorganic surface active agents.

2. The titania sol according to claim 1, containing 1 to 40 wt% of finely-divided titania in terms of TiO2.

3. The titania sol according to claim 1, wherein said water-soluble organic compound is at least one compound selected from water-soluble high molecular compounds, nonionic surface active agents, cationic surface active agents and polyhydric alcohols.

4. The titania sol according to claim 3, wherein said water-soluble high molecular compound is polyvinyl alcohol.

5. The titania sol according to claim 3, wherein said nonionic surface active agent is a polyoxyethylene alkyl phenyl ether derivative.

6. The titania sol according to claim 3, wherein said polyhydric alcohol is glycerin.

* * * * *